United States Patent
Sumian et al.

(10) Patent No.: US 6,287,549 B1
(45) Date of Patent: Sep. 11, 2001

(54) METHOD FOR REMOVING SUPERFLUOUS HAIRS

(75) Inventors: Chryslain Sumian; Frank Pitre, both of Antibes; Serge Mordon, Villeneuve d'Asq; Karine Buffard, Mougins; Martine Bouclier, Valbonne, all of (FR)

(73) Assignee: Centre International de Recherche Dermatologiques Galderma (C.I.R.D.) Galderma, Valbonne (FR)

( * ) Notice: Subject to any disclaimer, the term of this patent is extended or adjusted under 35 U.S.C. 154(b) by 0 days.

(21) Appl. No.: 09/402,351
(22) PCT Filed: Apr. 28, 1998
(86) PCT No.: PCT/FR98/00850
 § 371 Date: Dec. 22, 1999
 § 102(e) Date: Dec. 22, 1999
(87) PCT Pub. No.: WO98/48716
 PCT Pub. Date: Nov. 5, 1998

(30) Foreign Application Priority Data

Apr. 29, 1997 (FR) .................................................. 97 05297

(51) Int. Cl.⁷ .............................. A61K 7/155; A61K 7/15
(52) U.S. Cl. .................................................. 424/73; 606/9
(58) Field of Search .................................. 424/73; 606/9, 606/133

(56) References Cited

U.S. PATENT DOCUMENTS

| 5,425,728 | 6/1995 | Tankovich | 606/9 |
| 5,817,089 | * 10/1998 | Tankovich et al. | 606/9 |

FOREIGN PATENT DOCUMENTS

| 2 131 750 | 9/1994 | (CA) . |
| 0 375 520 | 6/1990 | (EP) . |

* cited by examiner

*Primary Examiner*—James M. Spear
(74) *Attorney, Agent, or Firm*—Burns, Doane, Swecker & Mathis, L.L.P.

(57) ABSTRACT

A method for eliminating unwanted hairs is provided. The method includes applying an effective amount of a composition including microparticles to the surface of the skin where the hairs are situated and removing the composition remaining on the surface of the skin. The microparticles contain chromophores and a second material different from the chromophores. At least 80% by weight of the microparticles have a diameter of between 3 $\mu$m and 10 $\mu$m. A composition containing a solvent which dissolves the chromophores may then be applied to the surface of the skin. Laser radiation is then applied in one or more shots. The emitted wavelength of the laser radiation is absorbed by the chromophores. The light energy and the emission duration of the laser energy are sufficient to damage and/or kill the cells responsible for the growth of the hair.

21 Claims, 3 Drawing Sheets

METHOD FOR REMOVING SUPERFLUOUS HAIRS

The invention relates to a method for preventing the regrowth of hairs and/or for eliminating hairs using a composition which is intended to be applied to the skin before a laser treatment and comprises microparticles of specific size comprising at least one chromophore.

It is known to use the laser technique in order to remove hairs. For example, U.S. Pat. Nos. 3,538,919 and 4,617,926 describe depilation methods using the light energy which is emitted by a laser and is transmitted by an optical fibre, which targets and eliminates the hairs one by one. Furthermore, U.S. Pat. No. 5,059,919 describes a depilation method using a laser placed at the orifice of the pilosebaceous unit whose light energy is absorbed by the melanin situated in the dermic papilla. These methods are time-consuming and may cause discomfort to the subject being treated, in particular due to the slowness of the method and the possible tugging on the hairs when they are put in place in order to be irradiated.

In order to solve the problem of the slowness of the methods described above, U.S. Pat. No. 5,425,728 then proposed irradiating a large area of the skin with a laser after application to this part of the skin of a composition comprising a chromophore exhibiting significant absorbence at the wavelength of the light emitted by the laser. This chromophore is more particularly carbon particles of average size between 10 and 20 nm. However, this method has certain drawbacks: the small size of these particles does not allow the pilosebaceous units to be penetrated deeply and selectively. This is because these particles may end up in the pores of the skins or alternatively in wrinkles, which causes an undesired lesion of parts of the skin during the irradiation. Furthermore, in spite of the use of ultrasound or prolonged massage, the carbon particles do not reach deeply into the pilosebaceous units. In order to increase the depth and the selectivity of the penetration of the particles in the pilosebaceous unit, the same author proposes, in Patent CA 2 131 750, a similar method using particles of carbon (graphite) of larger size (1 $\mu$m). In this method, the author describes the need to fracture the 1 $\mu$m carbon particles in order to allow them to penetrate to the bottom of the pilosebaceous units. In order to do this, it is necessary to apply 10 to 15 successive laser shots. Therefore, compared with the method described in U.S. Pat. No. 5,425,728, this method (described in Patent CA 2 131 750) improves the penetration in depth of the carbon particles into the pilosebaceous units, but has a major drawback: the fracture of a 1 $\mu$m carbon particle into two particles of smaller size is accompanied by the emission of a shockwave that propagates through the tissue. The need to apply 10 to 15 successive laser shots entails the emission of 10 to 15 shockwaves. However, a large number of shockwaves significantly increases the risks of irreversible lesions in the pilosebaceous units, as well as in the surrounding tissues (undesired effect). Furthermore, these methods only describe use of a Q switch-type laser (with emission time less than 50 $\mu$s), which implies that only the mechanical effect generated by the laser is used.

The object of the present invention is therefore to provide a depilation method which overcomes the drawbacks described above.

Its object is to provide a depilation method which makes it possible to target the pilosebaceous unit with particles:
that can be ionized in a small number of laser shots in the case of using a laser radiation of emission time less than 50 $\mu$s, which reduces the risks of irreversible lesions of the perifollicular tissues, that is to say those surrounding the follicle, while making it possible to damage and/or kill the cells responsible for the growth of the hair;
and/or
can convert the light energy of the laser radiation into heat energy, in the case of using a laser radiation of emission time longer than 50 $\mu$s, which reduces the risks of irreversible lesions of the perifollicular tissues, that is to say those surrounding the follicle, while making it possible to damage and/or kill the cells responsible for the growth of the hair.

These and other objects are achieved by the present invention, which relates to a method for preventing the regrowth of hairs and/or of eliminating hairs, characterized in that it comprises the following steps:

(1) a composition comprising, in a physiologically acceptable medium, microparticles of which at least 80% by weight have a diameter of between 3 $\mu$m and 10 $\mu$m, comprising chromophores, is applied to a surface of the skin, where the hairs are situated, (2) the composition applied in (1) which is still on the surface of the skin is removed, (3) optionally, a composition comprising a solvent which dissolves the chromophores used in step (1) is applied to the said surface of the skin, (4) at least one laser radiation is applied to the said surface of the skin in one or more shots, the emitted wavelength of which is absorbed by the chromophores of the composition applied in step (1) and the light energy and the emission duration of which are sufficient to damage and/or kill the cells responsible for the growth of the hair.

The diameter of the microparticles can be measured by scattering of light (Coulter counter) or by microscopy followed by image analysis.

The microparticles of determined diameters thus penetrate into the hair follicle but little through the corneal layer. This phenomenon is described in Patent EP 0375520. The microparticles selectively and progressively reach the follicular channel where the chromophores contained in these microparticles are ready to absorb the light emitted by the laser.

The microparticles may be of any kind and obtained by any known method.

They may be formed by polymers. In this case, they may be obtained after polymerization of monomers or after dispersion of synthetic or natural preformed polymers. The synthetic polymers that can be used may advantageously be selected from: polymers based on styrene, polyamides, polymers based on β-alanine, polymers derived from acrylic or methacrylic acid, polyesters derived from lactic and/or glycolic acid. The natural polymers may be selected from proteins (gelatin, albumin, casein, etc.) and polysaccharides (alginates, chitosan, etc.).

Mention may thus be made of the microparticles described in U.S. Pat. No. 4690825, WO 88/01164, EP 0391833, FR 2530250 and FR 2619385. More particularly, mention may be made of the Orgasol 2002 UD Nat Cos (Atochem) polyamide microparticles with particle size distribution centred on 5 $\mu$m (±1.5 $\mu$m) or the hollow Micropearl polymethyl methacrylate microcapsules of the company Seppic.

The microparticles used for the present invention may be formed by fatty substances. The fatty substances that can be used may advantageously be selected from derivatives of alcohols and of fatty acids, such as tristearin, semi-synthetic triglycerides or glycerol monostearate, and fatty alcohols such as cetyl alcohol. They preferably have a melting point above or equal to 50° C.

Vesicular microparticles may also be used as liposomes and, preferably, polymerized liposomes whether reverse or forward.

The methods for obtaining these microparticles (emulsifying, atomizing, microionizing in the case of chromophore particles etc.) may be adapted in order to obtain the desired particle size distribution by appropriately controlling their manufacturing process or by carrying out screening when the size distribution is broad. It is, for example, possible to adjust the size of the microparticles by selecting the polymerization solvent, the crosslinking agent or by modifying the stirring speed or time of the reaction medium. These various modifications belong to the prior art and/or are within the scope of the person skilled in the art.

The chromophores contained in the microparticles may be on the inside and/or on the surface of the microparticles, so long as their presence does not generate microparticles with a particle size distribution departing from the scope of the invention. These chromophores may form an integral part of the microparticle or alternatively be the microparticle itself. When the chromophores are the microparticle, these chromophores are preferably of density strictly less than 2.25 g/cm$^3$ (density of graphite particles).

The chromophores are preferably on the inside of the microparticles.

The chromophore or chromophores may be combined with the microparticles by any known means.

This combination may be carried out simultaneously with the formation of the microparticle, or after its formation. In the former case, mention may be made of the preparation of microspheres of polymers such as poly (D,L lactic acid/ glycolic acid) by the method of emulsifying/evaporating. In brief, the chromophores and the polymer are dissolved in an organic solvent that is immiscible with water. The solution is then emulsified in an aqueous phase with a surfactant. In the latter case, the procedure adopted may be to impregnate the microparticles with the aid of a solution containing the chromophores, such as may be the case with impregnating the Orgasol (Atochem) polyamide microparticles.

The chromophores may be any chemical entity which absorbs sufficiently at the wavelength in question, that is to say any chemical entity which, when it is contained in the composition applied according to the invention, makes it possible to convert the light energy which it absorbs into sufficient energy to damage and/or kill the cells responsible for the growth of the hair. More particularly, they may be of mineral origin, such as carbon black, graphite, red and black iron oxide, or of organic origin, such as melanin, indocyanine green, phthalocyanines and their metal complexes.

The microparticles comprising the chromophores may be dispersed in any medium which is physiologically acceptable and does not lead to the release of the said chromophores. The dispersing phase may be a hydrophilic or hydrophobic composition or an emulsion. The dispersing phase may thus, in particular, be in the form of a gel, milk, lotion, ointment, cream or salve.

A hydrophilic composition may be an aqueous gel or an aqueous-alcoholic gel. This may be obtained with the aid of a gelling agent, such as the crosslinked polyacrylic acid marketed under the brand name Carbopol® by the company Goodrich® or the cellulose derivatives marketed under the brand name Klucel® by the company Hercules®.

A hydrophobic composition may consist of oils such as acid esters, like fatty acid triglycerides, fatty alcohol esters, or their mixtures, alkanes, like liquid petroleum jelly, or else silicones.

In general, the composition according to the present invention comprises less than 40% by weight, and preferably contains from $10^{-4}$% to 40% by weight, of microparticles, at least 80% of which have a diameter of between 3 and 10 $\mu$m.

Preferably, at least 80% of the microparticles comprising at least one chromophore have a diameter of between 4 and 7 $\mu$m.

The application of the composition described in step (1) may be carried out by simple deposition or by a massage. Before step (1), depilation or shaving of the surface of the skin to be treated may be envisaged, in particular in order to make the hair follicles more accessible.

Step (2) of removing the composition applied in (1) which is still on the surface of the skin generally consists in a simple cleaning of the surface of the skin, and this cleaning is more particularly carried out with the vehicle (the medium) used for the composition used in (1).

The cleaning (2) makes it possible to take away the majority of the composition applied in (1) which has not penetrated into the pilosebaceous units (in particular inside creases and wrinkles).

The optional step (3) makes it possible to free the chromophores from the microparticles by dissolving and to make them penetrate more deeply into the hair follicle and/or be further dispersed in the hair follicle. This is particularly beneficial in the case of chromophores which are not in a particulate form, like in particular organic chromophores.

The solvents may, for example, be water, $C_1$ to $C_4$ alcohols, such as ethanol, propanol, isopropanol, 1-butanol, and esters such as ethyl acetate or butyl acetate.

According to the method of the present invention, any type of laser may be used, although a laser emitting light at a wavelength of between 350 nm and 2.5 $\mu$m is preferably used.

Examples of lasers which may be mentioned include Nd:YAG lasers (1064 nm or 532 nm), Ho:YAG lasers (2.12 $\mu$m), ruby lasers (694 nm) and dye lasers (585 nm) and diode lasers such as, for example, a diode laser (800 nm).

The light energy and the emission time which are sufficient to damage and/or kill the cells responsible for the growth of the hair can vary in a large extent as a function of the type of laser, chromophores selected and the composition comprising them.

Thus, when a light radiation is applied with a laser having an emission time less than or equal to 50 $\mu$s, the light energy applied is such that the chromophores are ionized, which generates shock waves that propagate in the tissues as far as the dermic papilla in order to damage and/or kill the cells responsible for the growth of the hair.

As we indicated above, one of the advantages of the invention is that it is not necessary to fraction the chromophores, as was the case in the prior art. The number of shots needed to ionize the chromophores is thus smaller, and this makes it possible to reduce the risks of irreversible lesions of the perifollicular tissues, that is to say the tissues which surround the hair follicle.

This number of shots is preferably less than 5. This is the case, for example, for nanometric carbon particles.

When a light radiation is applied with a laser having an emission time longer than 50 $\mu$s, the light energy applied is such that the chromophores convert the light energy emitted by the laser into heat energy, this heat energy then being transmitted by conduction as far as the dermic papilla in order to damage and/or kill the cells responsible for the growth of the hair.

Preferably, a laser having an emission time less than or equal to 50 $\mu$s is used.

Of course, the wavelength, the emission time and the light energy of the radiation of the laser are chosen as a function of the absorbence of the composition used comprising the chromophores. More particularly, as a function of the composition used comprising the chromophores, these parameters correspond to those allowing weak, or even zero absorption, of the light by the various constituents of the first layers of the skin, and significant absorption by the chromophore used, the aim of this being to avoid any irreversible lesion of the skin.

This significant absorption corresponds to that which is sufficient to damage and/or kill the cells responsible for the growth of the hair.

The undesired irreversible lesions of the skin correspond, in particular, to impairment of the capillary vessels lying in the dermis by coagulation of haemoglobin or irreversible destruction of melanocytes, Langerhans cells, keratinocytes or fibroblasts, in particular by volatilization of the endogenous chromophores contained in these cells or their precursors, such as water, melanin or proteins.

BRIEF DESCRIPTION OF THE DRAWINGS

FIG. 1 summarizes the structure of the pilosebaceous unit, the hairs being produced by the hair follicles A, cylindrical invaginations of the basal layer of the epithelium with surface surrounded by connective tissue.

Figure 1:
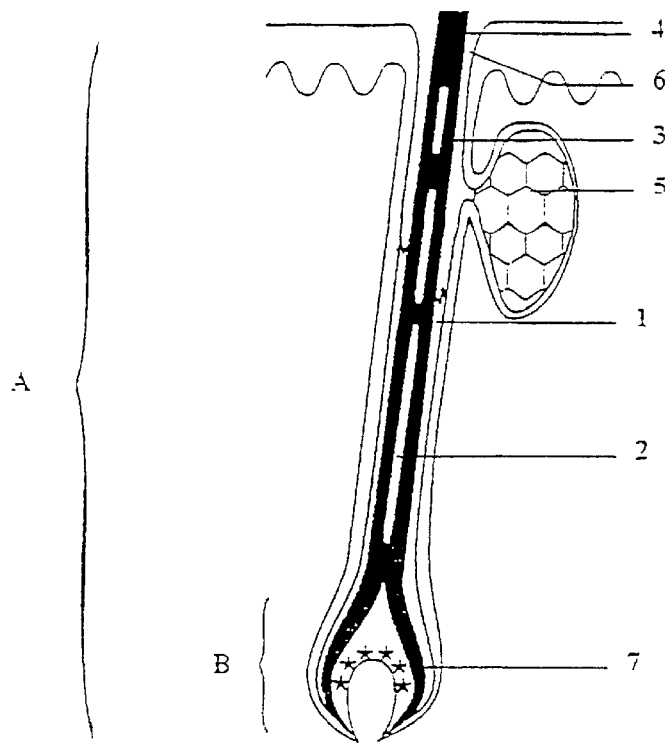
FIGS. 1 to 5 on sheets 1/3 to 3/3 allow the invention to be better illustrated, but without limiting its scope. These figures correspond to a diagrammatic representation of a pilosebaceous unit.

The hair grows inside the hair bulb B situated at the base of the follicles.

The hair follicle is a tubular structure consisting of five concentric layers of epithelial cells.

During the growth of the hair, the epithelial cells surrounding the dermic papilla proliferate to form the inner four layers of the follicle.

The bulb consists of epithelial cells with high mitotic power. At the bulb, all the layers fuse. During the growth of the hair, the epithelial cells surrounding the dermic papilla proliferate to form the inner four layers of the follicle.

As they progress from the hair bulb B to the skin surface, the inner three layers undergo keratinization to form the hair proper. The outer two layers form the outer epithelial sheath 1.

The cells of the innermost layer of the follicle undergo moderate keratinization leading to the formation of the medulla 2 at the heart of the hair. The medulla is surrounded by a thick layer, highly keratinzed, the cortex 3 which forms the most important part of the hair.

The third layer forms the cuticle 4, a thin hard layer coating surface of the hair.

The cells of the fourth layer of the follicle are only minorly keratinized. It disappears at the channels of the sebaceous glands 5 leaving a space, the ostium 6.

In the follicle which is growing, large active melanocytes are dispersed among the proliferative cells 7, which form the cortex of the hair and determine its colour.

Figure 2:
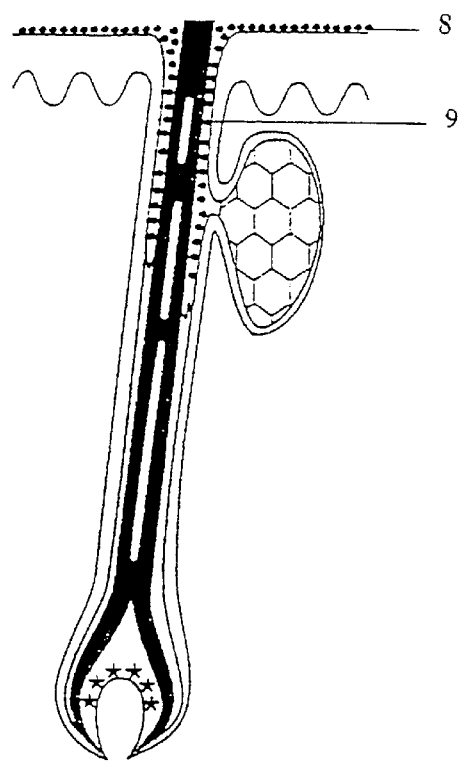

Application of the composition given by way of example below:

The composition described in this example is applied to the surface of the skin in excess (FIG. 2). After gentle massage for a few minutes, some of the microparticles 8 of calibrated size contained in the formulation will descend along the hair shaft into the ostium 9 to the level of the sebaceous glands.

Figure 3:
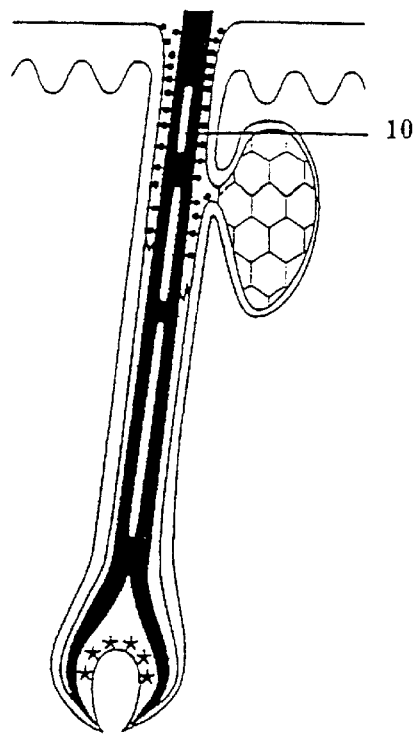

After having cleaned the surface of the skin with the vehicle of the formulation, FIG. 3, the microparticles loaded with exogenous chromophores 10 only remain in the ostium.

Laser Irradiation:

The laser used in this example is an Nd:YAG laser emitting a radiation of wavelength 1064 nm and having an emission time of 7–12 ns. At this wavelength, the radiation is absorbed very little by the various constituents of the first layers of the skin and is principally absorbed by the exogenous chromophore contained in the microparticles.

Figure 4:
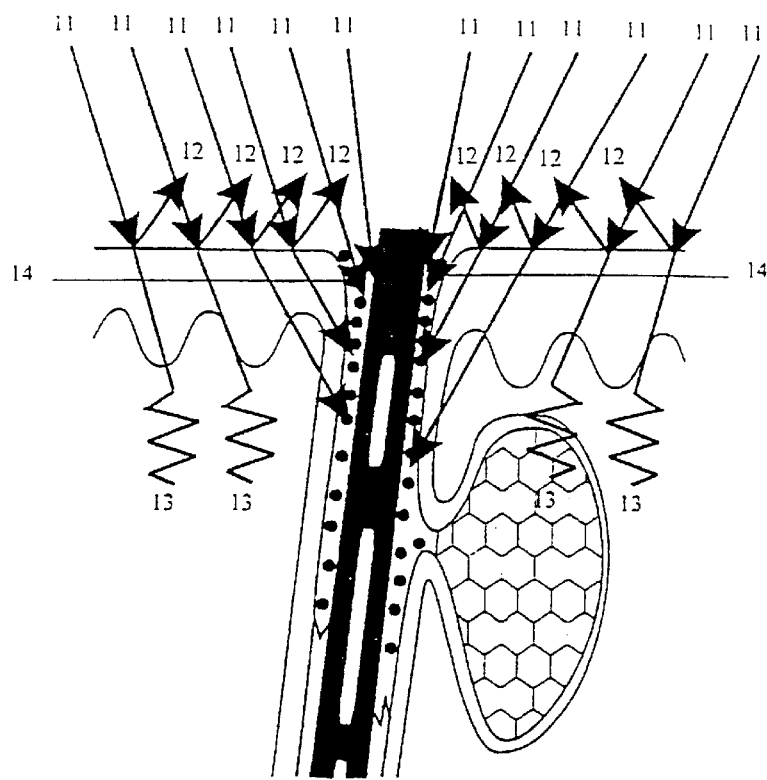

When using the following parameters: frequency: 5 Hz; diameter of the laser spot: 3 mm; energy per pulse: 200 mJ; scanning rate: 15 s per 1.5 $cm^2$; each 7 $mm^2$ area of skin receives an energy of 400 mJ. FIG. 4 shows the irradiation of the pilosebaceous unit where a small fraction of the energy delivered 11 is reflected 12 (5%) by the surface of the skin and another fraction transmitted. The photons transmitted into the skin are either scattered 13 (10%) or absorbed by the exogenous chromophore 14.

Figure 5A:
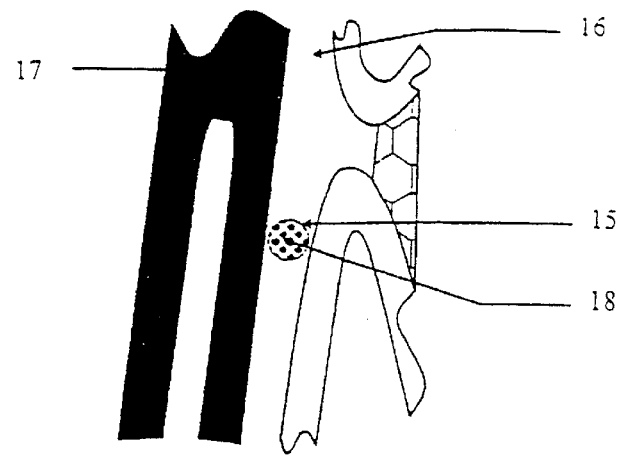
Figure 5B:
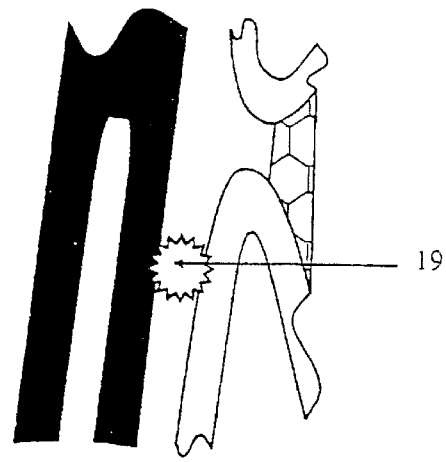
Figure 5C:
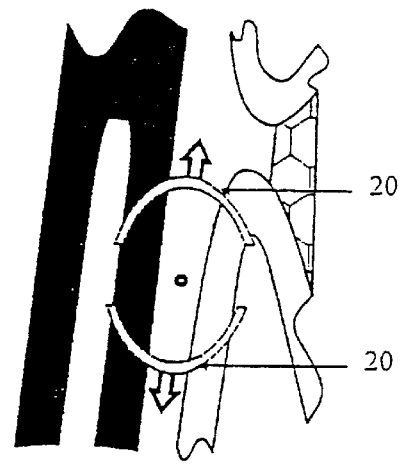

FIGS. 5A, 5B, 5C describe the interaction between the photons transmitted into the skin and a microparticle.

FIG. 5A shows a microparticle 15 placed in the ostium 16 situated around the hair shaft 17. The microparticles used, when they are not loaded with exogenous chromophores, absorb the employed wavelength little. The incorporation of carbon black particles 18 of particle size distribution centred around 13 nm in the microparticles of particle size distribution centred on 5 $\mu$m (±1.5 $\mu$m) makes it possible for fine particles absorbing strongly the wavelength used to be placed selectively in the pilosebaceous unit.

FIG. 5B describes the absorption of the photons transmitted into the skin by the carbon particles. Because of their small particle size distribution, the carbon particles sublime and form a plasma 19 in one to two laser shots. At the boundary between the plasma and the external medium (the ostium), FIG. 5C, a pressure gradient appears which induces the formation of a shockwave 20 that propagates in the adjacent tissues as far as the hair bulb in order to damage/eliminate the cells responsible for the growth of the hair.

| Composition example | % by mass |
|---|---|
| Part A: | |
| FW1 gas black (Degussa) | 0.2 |
| Parleam oil | 1.55 |
| Solsperse 21000 (ICI) | 0.05 |
| Orgasol 2002 UD Nat Cos (Elf Atochem) | 7.3 |
| Part B: aqueous gel | |
| Carbopol 980 (BF Goodrich) | 0.9 |
| 5% strength sodium hydroxide | 7.3 |
| Water | 82.7 |

In brief, the pigment is dispersed in the oily mixture, then the Orgasol microparticles are impregnated with the lipophilic dispersion, this constituting part A. The Orgasol microparticles thus loaded are then dispersed in the aqueous gel (corresponding to part B).

What is claimed is:

1. A method comprising the following steps:
   (1) applying an effective amount of a composition comprising microparticles to a surface of the skin where hairs are situated wherein at least 80% by weight of the microparticles have a diameter of between 3 $\mu$m and 10 $\mu$m and wherein the microparticles comprise chromophores (2) removing said composition applied in (1) from the surface of the skin, (3) optionally, applying a composition comprising a solvent which dissolves the chromophores used in step (1) to the surface of the skin, and (4) applying at least one laser radiation to said surface of the skin in one or more shots, the emitted wavelength of which is absorbed by the chromophores of the composition applied in step (1) and the light energy and the emission duration of which are sufficient to damage and/or kill the cells responsible for the growth of the hair.

2. The method according to claim 1, wherein the microparticles further comprise polymers.

3. The method according to claim 2, wherein the polymers comprise polymers based on styrene, polyamides, polymers based on β-alanine, polymers derived from acrylic or methacrylic acid, polyesters derived from lactic and/or glycolic acid, proteins or polysaccharides.

4. The method according to claim 1, wherein the microparticles further comprise fatty substances.

5. The method according to claim 1, wherein the microparticles further comprise liposomes.

6. The method according to claim 1, wherein the chromophores are on the inside or on the surface of the microparticles.

7. The method according to claim 1, wherein the chromophores are selected from the group consisting of carbon black, graphite, black or red iron oxide, melanin, indocyanine green, phthalocyanines and their metal complexes.

8. The method according to claim 1, wherein the composition comprises less than 40% by weight of microparticles.

9. The method according to claim 1, wherein at least 80% by weight of the microparticles comprising chromophores have a diameter of between 4 $\mu$m and 7 $\mu$m.

10. The method according to claim 1, wherein before step (1) said surface of the skin is depilated or shaved.

11. The method according to claim 1, wherein step (2) is carried out by cleaning said surface with the aid of the medium used in the composition of step (1).

12. The method according to claim 1, wherein the chromophore solvents used in step (3) are $C_1$ to $C_4$ alcohols.

13. The method according to claim 1, wherein the laser used in step (4) emits light at a wavelength of between 350 nm and 2.5 $\mu$m.

14. The method according to claim 1, wherein the laser comprises Nd:YAG lasers (1064 nm or 532 nm), Ho:YAG lasers (2.12 $\mu$m), ruby lasers (694 nm), dye lasers (585 nm) or diode lasers (800 nm).

15. The method according to claim 1, wherein when light radiation is applied in step (4) with a laser having an emission time less than or equal to 50 $\mu$s, the light energy applied is such that the chromophores are ionized, which generates shock waves that propagate in the tissues as far as the dermic papilla in order to damage and/or kill the cells responsible for the growth of the hair.

16. The method according to claim 1, wherein when light radiation is applied in step (4) with a laser having an emission time longer than 50 $\mu$s, the light energy applied is such that the chromophores convert the light energy emitted by the laser into heat energy, this heat energy then being transmitted by conduction as far as the dermic papilla in order to damage and/or kill the cells responsible for the growth of the hair.

17. A method comprising the following steps:
(1) applying an effective amount of a composition comprising microparticles to a surface of the skin where the hairs are situated, wherein at least 80% by weight of the microparticles have a diameter of between 3 $\mu$m and 10 $\mu$m and wherein the microparticles comprise chromophores and a second material different from the chromophores;

(2) removing said composition applied in (1) from the surface of the skin;

(3) optionally, applying a composition comprising a solvent which dissolves the chromophores used in step (1) to the surface of the skin; and (4) applying at least one laser radiation to said surface of the skin in one or more shots, the emitted wavelength of which is absorbed by the chromophores of the composition applied in step (1) and the light energy and the emission duration of which are sufficient to damage and/or kill the cells responsible for the growth of the hair.

18. The method of claim 1, wherein the microparticle consists of a chromophore.

19. The method according to claim 17, wherein the chromophores are selected from the group consisting of carbon black, graphite, black or red iron oxide, melanin, indocyanine green, phthalocyanines and their metal complexes.

20. The method according to claim 17, wherein the composition comprises less than 40% by weight of microparticles.

21. The method according to claim 17, wherein at least 80% by weight of the microparticles have a diameter of between 4 $\mu$m and 7 $\mu$m.

* * * * *